United States Patent [19]

Szantay et al.

[11] 4,432,982
[45] Feb. 21, 1984

[54] POLYCYCLIC COMPOUNDS SUBSTITUTED ON THE A-RING, PHARMACEUTICAL COMPOSITIONS CONTAINING THEM, AND METHODS OF TREATING PSORIASIS WITH THEM

[75] Inventors: Csaba Szantay; Lajos Szabo; Gyorgy Kalaus; Mari Zajer nee Balazs; Lilla Forgach; Egon Karpati; Arpad Kiraly; Gyöngyver Kiraly nee Soos; Laszlo Szporny; Bela Rosdy, all of Budapest, Hungary

[73] Assignee: Richter Gedeon Vegyeszeti Gyar Rt., Budapest, Hungary

[21] Appl. No.: 345,633

[22] Filed: Feb. 4, 1982

[30] Foreign Application Priority Data

Feb. 11, 1981 [HU] Hungary ................. 324/81

[51] Int. Cl.³ ................ A61K 31/435; C07D 461/00
[52] U.S. Cl. ........................... 424/256; 546/51
[58] Field of Search ................. 424/256; 546/51

[56] References Cited

U.S. PATENT DOCUMENTS

| | | | |
|---|---|---|---|
| 4,065,458 | 12/1977 | Lorincz et al. | 546/51 |
| 4,123,535 | 10/1978 | Pfäffli | 424/256 |
| 4,146,643 | 3/1979 | Pfäffli | 546/51 X |
| 4,328,231 | 5/1982 | Zajer nee Balazs et al. | 424/256 |

OTHER PUBLICATIONS

Arzneimittel Forschung, 26, No. 10, Rosdy et al., pp. 1921–1926.

Primary Examiner—Diana G. Rivers
Attorney, Agent, or Firm—Karl F. Ross; Herbert Dubno

[57] ABSTRACT

The invention relates to new polycyclic compounds substituted on the A-ring. More particularly, the invention concerns new polycyclic compounds of the formula (I)

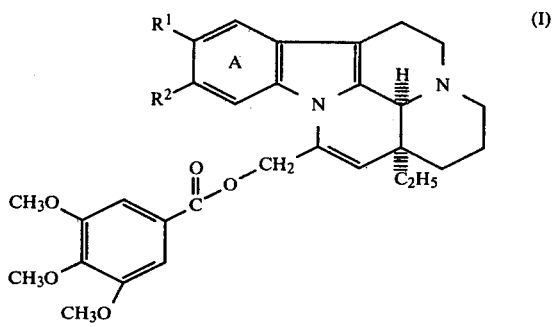

wherein
$R^1$ is methoxy or halogen and
$R^2$ is hydrogen; or
$R^1$ is hydrogen and
$R^2$ is halogen and acid addition salts thereof.

5 Claims, No Drawings

POLYCYCLIC COMPOUNDS SUBSTITUTED ON THE A-RING, PHARMACEUTICAL COMPOSITIONS CONTAINING THEM, AND METHODS OF TREATING PSORIASIS WITH THEM

The invention relates to new polycyclic compounds substituted on the A-ring. More particularly, the invention concerns new polycyclic compounds of the formula (I)

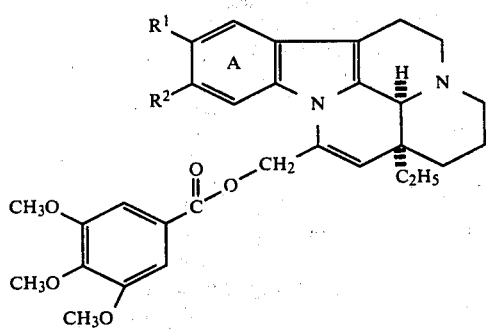

wherein
$R^1$ is methoxy or halogen and
$R^2$ is hydrogen; or
$R^1$ is hydrogen and
$R^2$ is halogen
and acid addition salts thereof.

According to another aspect of the invention there is provided a process for the preparation of compounds of the formula (I) in which $R^1$ and $R^2$ are as defined above, and acid addition salts thereof.

Still another aspect of the invention is a pharmaceutical composition having phosphodiesterase inhibiting activity, which comprises as active ingredient a pharmaceutically effective amount of a compound of the formula (I) or a pharmaceutically acceptable acid addition salt thereof with at least one pharmaceutically inert carrier or diluent.

According to the invention the compounds of the formula (I), wherein $R^1$ and $R^2$ have the same meaning as defined above, are prepared by reacting a corresponding compound of the formula (II)

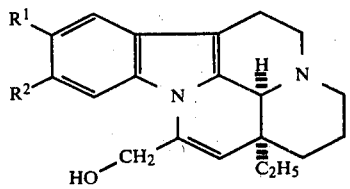

or a salt thereof, wherein $R^1$ and $R^2$ are as defined above, with 3,4,5-trimethoxy-benzoic acid or a derivative thereof capable of acylation, and if desired, converting a compound of the formula (I) obtained into an acid addition salt thereof.

The compounds of the formula (I) and (II) are new.

The term "halogen" throughout the specification refers to chlorine, bromine, fluorine or iodine, preferably chlorine or bromine, more preferably bromine.

The structurally closest compounds known in the art are 11-methoxy-apovincaminol (apovincinol) and trimethoxybenzoate salt thereof. The preparation of these compounds from naturally occuring vincine and their selective cerebral vasodilating activity are disclosed in the U.S. Pat. No. 4,065,458. The known compounds correspond to compounds of the formula (I) and (II), respectively, in which $R^1$ is hydrogen and $R^2$ is methoxy.

The new compound of the general formula (II), in which $R^1$ is methoxy and $R^2$ is hydrogen can be prepared from 10-methoxy-apovincamine, which was reported in the Published German Patent Application No. 2,458,164. Another method for the synthesis of this compound is described in Heterocycles 6(3), 321 (1977) by G. Kalaus et al.

The new compounds of the formula (II), in which $R^1$ is halogen, $R^2$ is hydrogen or $R^1$ is hydrogen and $R^2$ is halogen can be prepared from 10- or 11-halogen-apovincamine.

Though 10- and 11-halogen-apovincamines fall under the scope of the Published German Patent Application No. 2,458,164, up to now their preparation has not been specifically described. The preparation of 10- and 11-halogen-apovincamine is illustrated by Example 3 and 6, respectively of the present application.

Both the U.S. Pat. No. 4,065,458 and The Published German Patent Specification No. 2,458,164 describe compounds which influence the condition of the vessels, while the new compounds according to the invention inhibit phosphodiesterase enzyme activity and can primarily be used to treat skin diseases accompanied by a pathological cell proliferation or to prevent the recurrence of such diseases.

Skin diseases accompanied by a pathological proliferation of epidermis are relatively frequent and involve several percent of the population. Diseases of this kind include psoriasis.

Since some skin disease accompanied by a pathological proliferation does not occur on animals, e.g. psoriasis, the anti-psoriatic activity of the compounds can be predicted based upon animal experiments only indirectly.

Voorhees et al. [Arch. Derm. 104, 359–365 (1971)] established that the pathogenic proliferation of cells is accompanied by the decrease of the level of cyclic adenosine monophosphate (c-AMP). As it is well known, c-AMP is formed by adenyl cyclase and is decomposed under the effect of phosphodiesterase. Voorhees successfully influenced psoriasis by agents stimulating the activity of adenyl cyclase (e.g. noreepinephrine) or inhibiting the activity of phosphodiesterase (e.g. papaverine).

When planning our model experiments we set out from the assumption that the inverse of Voorhee's statement is also true, i.e. if a compound inhibits the activity of phosphodiesterase, this indirectly makes it probable that the compound is suitable for treating psoriasis or other skin diseases accompanied by a pathogenic cell proliferation. This assumption has been verified; the compound showing in vitro a phosphodiesterase inhibiting activity proved effective in the clinical treatment of psoriasis.

The model experiments were performed by means of phosphodiesterase isolated from animal tissues (rat brain, cattle brain, cattle heart). The enzyme was isolated by the technique of J. Schröder and H. V. Richenberg [Biochem. Biophys. Acta 302, 50 (1973)] whereupon the phosphodiesterase isolated was purified according to J. G. Hardman and E. W. Sutherland [J.

Biol. Chem. 240, 3704 (1965)] and the activity of the purified enzyme was measured by the radioisotope method developed by G. Pöch in the presence of an excess amount of tritium labeled c-AMP (10.1 mmoles of a c-AMP substrate containing 2.59K Bq of 3H-c-AMP), in an incubator. The measurement was first carried out without the inhibiting substance and then in the presence of one of the compounds of the general formula (I) as an inhibiting agent, after an incubation period of 20 minutes [N.S. Arch. Pharmacol. 268, 272 (1971)]. From the test compounds a 1 mmole stock solution was prepared with aqueous hydrochloric acid solution and different amounts were added to the enzyme preparates to give $5 \times 10^{-7}$, $1 \times 10^{-6}$, $1 \times 10^{-5}$, $5 \times 10^{-5}$ and $10^{-4}$ mole/lit. of the test compound. A solution of papaverine used as reference material was added to the enzyme preparate in an analogous manner.

The activity of the solutions containing the compounds of formula (I) and papaverine was expressed in percents of the control (enzyme solution without any inhibitor substance, the activity thereof was taken 100%). The results obtained on an enzyme isolated from cattle heart are as follows:

| Test compound (enzyme inhibitor) | the effect of a $5 \times 10^{-6}$ | $1 \times 10^{-5}$ | $5 \times 10^{-5}$ mole/lit. concentration of the test compound on enzyme activity in % of the control |
|---|---|---|---|
| 10-methoxy-apovincaminol-3',4',5'-trimethoxy-benzoate (in DMSO) | 59.1 | 40.3 | 21.3 |
| 10-bromo-apovincaminol-3',4',5'-trimethoxy-benzoate (in DMSO) | 67.8 | 61.8 | |
| /–/-11-bromo-apovincaminol-3',4',5'-trimethoxy-benzoate HCl (in water) | 31.9 | 21.8 | 21.8 |
| Papaverine HCl (in water or DMSO) | 91.3 | 82.7 | 43.7 |

The above results show that the activity of the three tests compounds essentially surpasses that of papaverine used for comparision.

The first clinical tests were carried out with preparations for topical use, e.g. ointments, creams, solutions, tinctures, pastes, aerosols, etc. containing the new compound according to the invention as an active ingredient. More particularly, creams containing 2%, 1%, 0.5%, 0.25% and 0.1% of a compound of the formula (I) were employed.

Clinical tests were performed on patients suffering from psoriasis. During the tests the patients have not received any systemic treatment, e.g. immunosuppressive, cytostatic or glucocorticoid treatment for their basic disease.

Groups of 5 were examined by the so called plaque method. One side of symmetrical skin lesions was treated by a cream containing the active ingredient in the desired concentration, while on the other side placebo was applied. The further psoriatic sites on the skin were subjected to other topical treatments for example with ointments containing flumethasone pivalate and salicyclic acid, as active ingredient, which are widely used for the treatment of psoriases.

The tests were started with creams having a higher active ingredient concentration and then further patients were treated with preparations containing the smallest effective active ingredient concentration. The skin was treated 2 to 3-times a day until the symptoms disappeared or were considerably improved (1 to 6 weeks).

The efficiency was evaluated upon observing three symptoms: inflammation, infiltration and desquamation (peeling). The intensity of the symptoms was qualified by scores between 0 and 3. The total number of scores served as a measure of the reduction of symptoms. The results were evaluated by methods of mathematical statistics. The tests unambiguously proved that the compositions described above can successfully be used for treating psoriasis. During the treatment undesirable side effects have never been observed.

According to the invention the new compounds of the formula (I), wherein $R^1$ and $R^2$ have the meanings defined above, are prepared from new compounds of the general formula (II), in which $R^1$ and $R^2$ are as defined above, or the salts thereof.

The new starting compounds of the general formula (II) are prepared from 10-methoxy-apovincamine disclosed in Heterocycles 6 (3), 321 (1977) or 10- or 11-bromo-apovincamine prepared as described in Examples 3 and 6, respectively, by selective reduction. As a reducing agent complex metal hydride, preferably lithium-aluminum hydride or sodium-dihydro-bis(2-methoxyethoxy)aluminate can be employed.

The compounds of the general formula (II) obtained are then reacted with 3,4,5-trimethoxy-benzoic acid or a derivative thereof capable of acylation to give compounds of the formula (I).

The acylation is carried out in the presence of an organic solvent, preferably benzene or a homolog thereof, a chlorinated hydrocarbon, aliphatic ketone or pyridine; preferably methylene chloride, chloroform and/or pyridine. If the reaction is performed with a 3,4,5-trimethoxy-benzoyl halide, preferably an acid binding agent is added to the reaction mixture in an amount equivalent with the halogenic acid formed or in a slight excess. As an acid binding agent for example alkali metal carbonates, alkali metal hydrocarbonates or organic basic amines, e.g. pyridine the latter used also as a solvent, may be employed. If the reaction is carried out with 3,4,5-trimethoxy-benzoic acid, a catalytic amount of an acid, preferably hydrochloric acid or sulfuric acid or a carboxylic group activator and/or a dehydrating agent is added to the reaction mixture. As a carboxylic group activator for example halogeneted phenols, preferably pentachlorophenol, as a dehydrating agent for instance N,N'-dicyclohexyl-carbodiimide may be employed. The acylation is accomplished at a temperature between −20° C. and the boiling temperature of the reaction mixture, preferably between 20° C. and 60° C.

The product is isolated from the reaction mixture by extraction and/or evaporation.

If desired, the product obtained is converted into an acid addition salt, preferably a pharmaceutically acceptable acid addition salt thereof. Inorganic acid addition salts include e.g. chlorohydrate, sulfate and phosphate salts, while typical organic acid addition salts are the hydrogen tartarate, succinate, citrate and ascorbate. When preparing salts an alcoholic, ethereal or acetonic solution of the acid component is added to the product. The salts are prepared at a pH of 3 to 6.

The pharmaceutical compositions contain 0.1 to 8.0% by weight, preferably 0.2 to 2.0% by weight of an active ingredient of the formula (I). The compositions may contain also further pharmaceutically active substances, e.g. antibiotics, cytostatics, prostaglandins, ditranol, salicylic acid, tar, antiinflammatory substances, immunosupressants glucocorticoids and in case of parenteral administration local anaesthetics.

As glucocorticoid preferably triamcinolonacetonide is used. Preferably formulations suitable for topical, local use, such as creams, ointments, solutions, gelees, aerosols, aerosol foams, plasters, etc. are prepared.

Though the active ingredient is preferably employed as a base, its pharmaceutically acceptable acid addition salts, such as hydrogen tartarate or hydrochloride, etc. may also be used.

The active ingredient is preferably incorporated into creams easy to wash down.

When preparing creams the active ingredient is dissolved in an alcoholic solvent, preferably propylene or dipropylene glycol or a mixture thereof with a small amount of water, and the solution is admixed with a well smearable skin compatible fatty phase.

The fatty phase may contain cetyl, stearyl, cetostearyl alcohol, paraffin oil, glycerin monostearate, etc.

The creams may further contain emulsifying agents, preferably polyoxyethylene-sorbitane monooleate or monostearate and as a preservative various benzoic acid derivatives, preferably p-hydroxy-benzoic acid methyl ester.

The cream obtained preferably contains 0.25 to 2.5% by weight of active ingredient, 45 to 50% by weight of glycol, 23 to 27% by weight of paraffin oil, 11 to 15% by weight of stearyl alcohol and further additives up to 100%.

The active substance optionally may be employed also as an ointment, which cannot be washed down with water. In this case the active ingredient is directly incorporated into the fatty phase.

The solutions prepared from the compounds according to the invention or acid addition salts thereof contain for example 20 to 40% by weight of propylene glycol or dipropylene glycol as a solvent, 40 to 55% by weight of a 96% ethanol and distilled water up to 100%.

If aerosol preparations are to be prepared, to a solution of the active ingredient or an acid addition salt thereof in propylene glycol a fat, preferably isopropyl myristate, and a propellant, preferably freon, are added.

Aerosol foams may for example be prepared by adding an alcoholic solution of the active ingredient or an acid addition salt thereof to a mixture of 0.5 to 1,5% by weight of cetostearyl alcohol, 1 to 3% by weight of benzyl alcohol, 15 to 20% by weight of polyoxyethylene-sorbitane monooleate or monostearate and 25 to 30% by weight of water followed by the addition of a propellant, for example freon.

For parenteral administration, preferably for subcutaneous or intracutaneous administration injection solutions are generally prepared. In this case a salt of the active ingredient is dissolved in a 0.72% aqueous sodium chloride solution and the pH of the solution is adjusted to 5.

Further details of the invention are illustrated by the following examples which are not intended to limit the scope of protection in any way.

EXAMPLE 1

10-Methoxy-apovincaminol 0.6 g. (1.64 mmoles) of 10-methoxy-apovincamine are dissolved in 18 ml. of absolute benzene and 0.8 ml. of sodium dihydro-bis[2-methoxyethoxy]aluminate are added to the solution at room temperature, with stirring, whereupon stirring is continued for a further one hour. When the reaction is complete, 2 ml. of ethyl acetate are added to the reaction mixture which is then evaporated in vacuo. The evaporation residue is dissolved in 15 ml. of a 2.5 ml of a 2.5% aqueous sulfuric acid solution, the pH is adjusted to 10 with a 40% aqueous sodium hydroxide solution under cooling and is extracted subsequently with 15 ml., 10 ml. and 5 ml of dichloromethane. The organic phase is dried with magnesium sulfate, filtered and the filtrate is evaporated in vacuo. The oily residue is crystallized from acetonitrile.

Yield: 0.45 g. (81.2%) of the named compound

Melting point: 148° to 150° C.

Formula: $C_{21}H_{26}N_2O_2$.

Molecular weight: 338.45.

IR spectrum (KBr): $\nu_{max}$ 1642 1603 cm$^{-1}$ (=C=C=)

$^1$H-NMR spectrum (CDCl$_3$):

δ: 0.94 (t, 3H C$\underline{H}_3$CH$_2$—)

δ: 2.90 (s, 1H, HO—)

δ: 3.84 (s, 3H, CH$_3$O—)

δ: 4.10 (s, 1H, fused H)

δ: 4.55–4.75 (q, 2H, HO—C$\underline{H}_2$—)

δ: 5.03 (s, 1H, =C=CH—)

δ: 6.81–7.56 (m, 3H, aromatic H)

Mass spectrum (e/m): 338/26/, 309/89/, 307/5/, 290/8/, 268/100/, 2 66/38/, 237/21/, 208/10/, 115/9/, 77/14/, 43/64/, 30/14/.

EXAMPLE 2

10-Methoxy-apovincaminol-3',4',5'-trimethoxybenzoate 0.45 g. (1.33 mmoles) of 10-methoxy-apovincaminol are dissolved in 10 ml. of absolute dichloromethane and to the solution 0.45 g. of anhydrous sodium carbonate and 0.34 g. (1,48 mmoles) of 3,4,5-trimethoxy-benzoyl chloride are added to the solution, which is then stirred for 24 hours at room temperature. The reaction mixture is diluted with 15 ml. of water, the organic phase is separated, the aqueous phase is extracted with two 5 ml. portions of dichloromethane. The combined dichloromethane solution is dried with magnesium sulfate, filtered and the filtrate is evaporated in vacuo. The evaporation residue is crystallized from methanol.

Yield: 0.45 g. (63,1%) of the title compound.

Melting point: 167° to 168° C.

Formula: $C_{31}H_{36}N_2O_6$.

Molecular weight: 532.63.

IR spectrum (KBr): $\nu_{max}$ 1725 cm$^{-1}$ (=C=O) 1655 cm$^{-1}$ (=C=C=)

$^1$H-NMR spectrum/CDCl$_3$/:

δ: 0.97 (t, 3H, C$\underline{H}_3$CH$_2$—)

δ: 3.73 (s, 6H, CH$_3$O—)

δ: 3.83 (s, 6H, CH$_3$O—)

δ: 4.17 (s, 1H, fused H)

δ: 5.23 (s, 1H, =C=CH—)

δ: 5.27–5.45 (q, 2H, —OCH$_2$—)

δ: 6.70–7.52 (m, 5H, aromatic H)

Mass spectrum (m/e/): 532(33), 501(100), 462(91), 322/20/, 307/8/, 292/85/, 252/50/.

EXAMPLE 3

10-Bromo-apovincaminol 1.50 g. (3.61 mmoles) of 10-bromo-apovincamine are dissolved in 45 ml. of absolute benzene and 4.5 ml. of sodium dihydro-bis(2-methoxyethoxy)-aluminate (REDAL) is added to the solution dropwise, with stirring, at room temperature. Stirring is continued for further 2 hours, whereupon 10 ml. of ethyl acetate are added to the reaction mixture which is then evaporated in vacuo. The residue is dissolved in 150 ml. of a 2.5% aqueous sulfuric acid solution and its pH is adjusted to 10 with a 40% aqueous sodium hydroxide solution under outer cooling. The reaction mixture is extracted subsequently with 120 ml., 110 ml. and 100 ml. of dichloromethane. The organic phase is dried with magnesium sulfate, filtered and the filtrate is evaporated in vacuo. The oily residue obtained, weighing 1.8 g. is crystallized from 10 ml. of methanol.

Yield: 1.10 g. (78.4%) of the named compound.
Melting point: 178° to 180° C.
Analysis for $C_{20}H_{24}BrN_2O$ (388.33): calculated: C, 61.86%, H, 6.23%, N, 7.22%; found: C, 61.92%, H, 6.43%, N, 6.82%.

IR spectrum (KBr): $\nu_{max}$ 1630 $cm^{-1}$ (=C=C=)

$^1$H-NMR spectrum (CDCl$_3$):
δ: 0.96 (m, 3H, $\underline{CH_3}CH_2$—)
δ: 2.0 (s, 1H, —OH)
δ: 4.12 (s, 1H, fused H)
δ: 4.56–4.75 (m, 2H, HO—$\underline{CH_2}$—)
δ: 5.12 (s, 1H, —CH=)
δ: 7.24–7.56 (m, 3H, aromatic H)

Mass spectrum/m/e/: 386/47/, 388/48/, 369/2/, 371/3/, 357/96/, 359/95/, 339/8/, 341/6/, 316/100/, 318/88/, 237/13/.

10-bromo-vincamine used as a starting compound was prepared as described hereinbelow:

4.60 g. (10.6 mmoles) of 10-bromo-vincamine are refluxed in 92 ml. of acetic anhydride for 20 hours. The dark brown reaction mixture is evaporated in vacuo, the residual oil is admixed with 150 ml. of water and its pH is adjusted to 11 with a 40% aqueous sodium hydroxide solution. It is shaken with 80 ml., 70 ml. and 60 ml. of dichloromethane, the organic phase is dried with magnesium sulfate, filtered and the filtrate is evaporated in vacuo. The evaporation residue is crystallized from 15 ml. of methanol.

Yield: 3.60 g. (81.7%) of 10-bromo-apovincamine.
Melting point: 163° to 165° C.
Analysis for $C_{21}H_{23}BrN_2O_2$ (415.33): calculated: C, 60.73%, H, 5.58%, N, 6.75%; found: C, 60.74%, H, 5.54%, N, 6.69%.

IR spectrum (KBr): $\nu_{max}$ 1718 $cm^{-1}$ /=C=O/
1620 $cm^{-1}$ /=C=C=/

$^1$H-NMR spectrum (DMSO-d6):
δ: 0.94 (t, 3H $\underline{CH_3}CH_2$—)
δ: 1.85 (q, 2H $CH_3\underline{CH_2}$—)
δ: 3.89 (s, 3H, —OCH$_3$)
δ: 4.05 (s, 1H fused H)
δ: 6.18 (s, 1H, =C=CH—)
δ: 7.17–7.57 (m, 3H, aromatic H)

Mass spectrum (m/e/): 417/35/, 415/36/, 388/100/, 386/99/, 347/90/, 345/95/, 331/8/, 329/9/, 306/99/, 187/6/.

EXAMPLE 4

10-Bromo-apovincaminol-3',4',5'-trimethoxy-benzoate 0.50 g. (1.29 mmoles) of 10-bromo-apovincaminol are dissolved in 15 ml. of absolute pyridine and to the solution 0.4 g. (1.74 mmoles) of 3,4,5-trimethoxy-benzoyl chloride are added. The reaction mixture is allowed to stand at room temperature for 24 hours. It is evaporated in vacuo and the oily residue is triturated with a 5% aqueous sodium hydrocarbonate solution (30 ml.). The solidifying substance is filtered off, washed with 15 ml. of water and recrystallized from 5 ml. of methanol.

Yield: 0.55 g. (73.5%) of the named compound.
Melting point: 121° to 122° C.
Analysis for $C_{30}H_{33}BrN_2O_5$ (581.49): calculated: C, 61.96%, H, 5.72%, N, 4.82%; found: C, 62.07%, H, 5.81%, N, 4.90%.

IR spectrum (KBr): $\nu_{max}$ 1705 $cm^{-1}$ (=C=O)
1640 $cm^{-1}$ /=C=C=/

$^1$H-NMR spectrum (CDCl$_3$):
δ: 1.00 (t, 3H, $\underline{CH_3}CH_2$—)
δ: 3.73 (s, 6H, 2x—OCH$_3$)
δ: 3.86 (s, 3H, —OCH$_3$)
δ: 4.16 (s, 1H, fused H)
δ: 5.2–5.5 (m, 3H, —OCH$_2$—+—CH=)
δ: 7.1–7.6 (m, 5H, aromatic H)

Mass spectrum (m/e): 580/39/, 582/38/, 551/100/, 553/98/, 510/86/, 512/79/, 370/19/, 372/14/, 340/33/, 342/25/, 300/23/, 302/19/, 281/26/, 212/23/, 207/20/.

EXAMPLE 5

10-Bromo-apovincaminol-3',4',5'-trimethoxy-benzoate hydrogen tartarate

The product of Example 4 is dissolved in diethyl ether and to the solution diethyl ether saturated with D-tartaric acid is added until the precipitation of hydrogen tartarate salt is complete.

Melting point: 118° to 120° C.
Molecular weight: 731.58.
IR spectrum (KB) $\nu_{max}$ 1710 $cm^{-1}$ (=C=O)

EXAMPLE 6

(−)-11-Bromo-apovincaminol

From 0.40 g. (0.88 mmoles) of (+)-11-bromo-apovincamine hydrochloride the free base is set free by partition between 5 ml. of dichloromethane and a 5% aqueous sodium carbonate solution. The organic phase is separated, dried with magnesium sulfate, filtered and the filtrate is evaporated to dryness in vacuo. The residue is dissolved in 5 ml. of absolute tetrahydrofurane. The latter solution is added to a suspension of 0.10 g. of lithium-aluminum hydride in 10 ml. of absolute tetrahydrofurane at room temperature, under continuous solution. Stirring is continued for further 2 hours and the excess of the reactant is decomposed by adding 2.5 ml. of ethyl acetate. The inorganic precipitate is eliminated by filtration and the filtrate is evaporated to dryness in vacuo. The residue is dissoled in 15 ml. of a 2.5% aqueous sulfuric acid solution, its pH is adjusted to 8 by a concentrated aqueous ammonium hydroxide solution and it is then extracted with three 5-ml. portions of dichloromethane. The combined organic phases are dried with magnesium sulfate, filtered and from the filtrate the solvent is eliminated by distillation. The residue can be used in the subsequent reaction step without purification.

Yield: 0.26 g. (76.5%) of the named compound.
Mass spectrum (m/e %): 386/M$^+$, $C_{20}H_{23}N_2OBr$, 100/; 385/53/; 371/8.9/; 357/80/; 330/31/; 329/26/; 328/25/; 327/16/; 316/23/; 300/16/; 286/27/; 271/12/; 249/10/;

$[\alpha]_D = -120.3°$; $[\alpha]_{546} = -144.2°$ (c=1.07; dichloromethane)

The starting compound of this example was prepared as follows:

1.00 g. of (+)-11-bromo-14-oxo-15-hydroxyimino-E-homoeburnane hydrochloride (2.21 mmoles) prepared according to the British Patent Specification No. 2,036,721 are heated in a mixture of 37.2 ml. of absolute methanol and 13.5 ml. of concentrated sulfuric acid in a bath of 125° C. for 8 hours. The reaction mixture is then poured onto 20 ml. of ice-cooled water and the pH of the solution is adjusted to 8 with a concentrated aqueous ammonium hydroxide solution. The mixture is extracted with three 8-ml. portions of dichloromethane, the combined organic phases are dried with magnesium sulfate, filtered and from the filtrate the solvent is eliminated in vacuo. The residue (0.88 g.) is dissolved in 3 ml. of acetone, the pH of the solution is adjusted to 4 with acetone in hydrochloric acid and the solvent is distilled off in vacuo. The residue is crystallized from 3 ml. of acetone.

Yield: 0.60 g. (60%) of (+)-11-bromo-apovincamine hydrochloride.

Melting point: 228° C. (acetone)

IR spectrum (KBr): 1730 (ester CO); 1638 (C=C); 1610 cm$^{-1}$ (aromatic).

Mass spectrum (m/e, %): 414/M+, $C_{21}H_{23}N_2O_2Br$, 41/; 385/100/; 356/9.2/; 342/13/; 329/13/; 329/10/; 306/13/; 265/13/; 204/8.6/; 191/9.8/;

$[\alpha]_D = +37.6$; $[\alpha]_{546} = +46.2°$ (c=0.35; dichloromethane).

EXAMPLE 7

(−)-11-Bromo-apovincaminol-3',4',5'-trimethoxy-benzoate hydrochloride 0.15 g. (0.39 mmoles) of (−)-11-bromo-apovincaminol are dissolved in 2 ml. of absolute pyridine and to the solution of 0.1 g. (0.43 mmoles) of freshly distilled 3,4,5-trimethoxy-benzoyl chloride are added. The reaction mixture is allowed to stand at room temperature for a day. Thereafter 0.2 ml. of water are added and the mixture is stirred for 30 minutes. The solvent is eliminated in vacuo, the residue is partitioned between 5 ml. of dichloromethane and 3 ml. of a 5% aqueous sodium carbonate solution. The organic phase is separated, dried with magnesium sulfate, filtered and the filtrate is evaporated to dryness in vacuo. The residue (0.22 g.) is dissolved in 1 ml. of acetone, the pH of the solution is adjusted to 4 with methanol in hydrochloric acid and the precipitated crystals are filtered off.

0.15 g. (62.6%) of the named compound are obtained.

Melting point: 157° to 159° C. (acetone).

IR spectrum/KBr/: 1712 (ester CO); 1645/C=C; 1585 cm$^{-1}$ (aromatic).

Mass spectrum (m/e, %): 580/M+, $C_{30}H_{32}N_2O_5Br$, 45/; 565/0.8/; 551/100/; 510/78/; 369/14/; 339/35/; 299/17/; 256/13/; 255/13/; 212/19/.

The rotatory power of the base set free from the hydrochloride is as follows: $[\alpha]_D = -53.5°$; $[\alpha]_{546} = 62.5°$ (c=0.78; dichloromethane).

EXAMPLE 8

| (−)-11-bromo-apovincaminol-3',4',5'-trimethoxy-benzoate | 2 g. |
|---|---|
| propylene glycol | 50 g. |
| paraffin oil | 26 g. |
| polyethylene glycol 400 | 5 g. |
| stearyl alcohol | 15 g. |
| glycerine monostearate | 2 g. |

The active ingredient is dissolved in propylene glycol on a water bath of a temperature not exceeding 50° C. The other components are melted and cooled to 40° to 45° C. under continuous stirring. To the melt the solution of the active ingredient is added under stirring and the cream obtained is stirred until it cools down.

Creamss containing 0.25, 0.5, 1.0 and 1.5% by weight of active ingredient are prepared in an analogous way.

EXAMPLE 9

Following the procedure described in Example 8 but replacing (−)-11-bromo-apovincaminol-3',4',5'-trimethoxy-benzoate by 10-bromo- or 10-methoxy-apovincaminol-3',4',5'-trimethoxy-benzoate creams are prepared.

EXAMPLE 10

| (−)-11-bromo-apovincaminol-3',4',5'-trimethoxy-benzoate | 2 g. |
|---|---|
| triamcinolone acetonide | 0.1 g. |
| propylene glycol | 49.9 g. |
| paraffin oil | 26 g. |
| polyethylene glycol 400 | 5 g. |
| stearyl alcohol | 15 g. |
| glycerin monostearate | 2 g. |

The procedure described in Example 8 is followed except that in this case two active substances are dissolved in propylene glycol.

Creams containing 10-bromo- or 10-methoxy-apovincaminol-3',4',5'-trimethoxy-benzoate as an active ingredient can be prepared in an analogous way.

EXAMPLE 11

| (−)-11-bromo-apovincaminol-3',4',5'-trimethoxy-benzoate.HCl | 1% |
|---|---|
| propylene glycol | 30% |
| 96% ethanol | 57% |
| distilled water | ad 100% |

A tincture is prepared using the above ingredients. If desired, the tincture can contain also 0.1% of triamcinolone acetonide.

EXAMPLE 12

| (−)-11-bromo-apovincaminol-3',4',5'-trimethoxy-benzoate.HCl | 0.5% |
|---|---|
| propylene glycol | 30% |
| isopropyl myristate | 4.5% |
| freon | 65% |

An aerosol is prepared using the above ingredients.

EXAMPLE 13

| (−)-11-Bromo-apovincaminol-3',4',5'-trimethoxy-benzoate.HCl | 2% |
|---|---|
| cetostearyl alcohol | 1% |
| benzyl alcohol | 2% |
| polyoxyethylene sorbitane monostearate | 15% |
| 96% ethanol | 30% |
| freon | 20% |

| | |
|---|---|
| -continued | |
| distilled water | ad 100% |

An aerosol foam is prepared using the above ingredients.

We claim:

1. A compound of the formula (I)

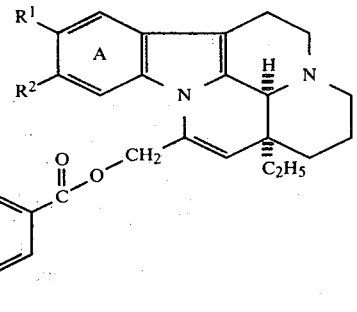

wherein
R[1] is halogen and
R[2] is hydrogen; or
R[1] is hydrogen and R[2] is halogen, or a pharmaceutically acceptable acid addition salt thereof.

2. The compound defined in claim 1 wherein R[1] is hydrogen and R[2] is halogen, or a pharmaceutically acceptable salt thereof.

3. 11-bromo-apovincaminol-3′,4′,5′-trimethoxy-benzoate or a pharmaceutically acceptable acid addition salt thereof as defined in claim 1.

4. An anti-psoriasis composition which comprises as active ingredient a pharmaceutically effective amount of the compound defined in claim 1 or a pharmaceutically acceptable acid addition salt thereof along with a pharmaceutically acceptable inert carrier.

5. A method of treating psoriasis which comprises the step applying to the skin to be treated a pharmaceutically effective amount of the compound defined in claim 1 or a pharmaceutically acceptable salt thereof.

* * * * *